(12) United States Patent
Nissing et al.

(10) Patent No.: US 6,180,214 B1
(45) Date of Patent: Jan. 30, 2001

(54) WIPING ARTICLE WHICH EXHIBITS DIFFERENTIAL WET EXTENSIBILITY CHARACTERISTICS

(75) Inventors: Nicholas James Nissing; David William Cabell, both of Cincinnati, OH (US)

(73) Assignee: The Procter & Gamble Company, Cincinnati, OH (US)

( * ) Notice: Under 35 U.S.C. 154(b), the term of this patent shall be extended for 0 days.

(21) Appl. No.: 09/231,002

(22) Filed: Jan. 14, 1999

Related U.S. Application Data

(60) Provisional application No. 60/073,443, filed on Feb. 2, 1998.

(51) Int. Cl.⁷ ....................................................... B32B 27/14
(52) U.S. Cl. ............................................ 428/195; 428/211
(58) Field of Search ..................................... 428/195, 211

(56) References Cited

U.S. PATENT DOCUMENTS

| | | |
|---|---|---|
| 1,819,041 | 8/1931 | Sherman . |
| 3,301,746 | 1/1967 | Sanford et al. ...................... 162/113 |
| 3,375,156 | 3/1968 | Edgar, Jr. ............................. 162/132 |
| 3,546,056 | 12/1970 | Thomas ................................. 161/57 |
| 3,597,299 | 8/1971 | Thomas et al. ....................... 161/57 |
| 3,615,976 | 10/1971 | Endres et al. ......................... 156/83 |
| 3,650,882 | 3/1972 | Thomas ............................... 161/122 |
| 3,673,026 | 6/1972 | Brown . |
| 3,684,641 | 8/1972 | Murphy ............................... 161/129 |
| 3,695,985 | 10/1972 | Brock et al. ........................ 161/129 |
| 3,708,383 | 1/1973 | Thomas et al. ....................... 161/57 |
| 3,709,750 | 1/1973 | Minshell ............................... 156/72 |
| 3,755,062 | 8/1973 | Schirmer ............................. 161/146 |
| 3,925,127 | 12/1975 | Yoshioka ............................. 156/85 |
| 3,929,135 | 12/1975 | Thompson ........................... 128/287 |
| 3,953,638 | 4/1976 | Kemp .................................. 428/154 |
| 3,994,771 | 11/1976 | Morgan et al. ..................... 162/113 |
| 4,300,981 | 11/1981 | Carstens ............................. 162/109 |
| 4,324,246 | 4/1982 | Mullane et al. .................... 128/287 |
| 4,342,314 | 8/1982 | Radel et al. ........................ 128/287 |
| 4,440,597 | 4/1984 | Wells et al. ........................ 162/111 |
| 4,463,045 | 7/1984 | Ahr et al. ........................... 428/131 |
| 4,469,735 | 9/1984 | Trokhan ............................. 428/154 |
| 4,522,863 | 6/1985 | Keck et al. ........................ 428/196 |
| 4,525,407 | 6/1985 | Ness .................................. 428/138 |
| 4,529,480 | 7/1985 | Trokhan ............................. 162/109 |
| 4,637,819 | 1/1987 | Ouelette et al. ................... 604/369 |
| 4,637,859 | 1/1987 | Trokhan ............................. 162/109 |
| 4,661,389 | 4/1987 | Mudge et al. ..................... 428/110 |
| 4,695,422 | 9/1987 | Curro et al. ....................... 264/504 |
| 4,778,644 | 10/1988 | Curro et al. ....................... 264/557 |
| 4,839,216 | 6/1989 | Curro et al. ....................... 428/134 |
| 4,847,134 | 7/1989 | Fahrenkrug et al. .............. 428/138 |

(List continued on next page.)

FOREIGN PATENT DOCUMENTS

| | | |
|---|---|---|
| 0 353 014 | 1/1990 | (EP) . |
| 1276228 | 2/1972 | (GB) . |
| WO 97/47809 | 12/1997 | (WO) . |

* cited by examiner

Primary Examiner—Newton Edwards
Assistant Examiner—J. M. Gray
(74) Attorney, Agent, or Firm—Joan B. Tucker; Roddy M. Bullock; David M. Weirich

(57) ABSTRACT

The present invention provides a disposable wiping article. The wiping article may be single-layer (single-ply), or multi-layer (multi-ply). At least one layer (the only layer in a single-layer wiping article) is a primary layer and is wet extensible. A discontinuous coating is applied to selected portions of the wet extensible primary layer and cured to form a constraining component which inhibits wet extension of the primary layer in the plane of the primary layer. As a result, the primary layer deforms, such as by buckling or puckering, in the Z-direction (perpendicular to the plane of the primary layer), resulting in increased caliper, bulk, and texture. In one embodiment, more than one primary layer may be used in a single wiping article.

18 Claims, 2 Drawing Sheets

U.S. PATENT DOCUMENTS

| | | | |
|---|---|---|---|
| 4,891,258 | 1/1990 | Fahrenkrug | 428/138 |
| 4,919,756 | 4/1990 | Sawdai | 162/111 |
| 5,006,394 | 4/1991 | Baird | 428/138 |
| 5,073,235 | 12/1991 | Trokhan | 162/199 |
| 5,223,096 | 6/1993 | Phan et al. | 162/158 |
| 5,227,228 | 7/1993 | Newell | 428/224 |
| 5,245,025 | 9/1993 | Trokhan et al. | 536/56 |
| 5,277,761 | 1/1994 | Phan et al. | 162/109 |
| 5,364,504 | 11/1994 | Smurkoski et al. | 162/116 |
| 5,401,557 | 3/1995 | Inomata et al. | 428/110 |
| 5,503,715 | 4/1996 | Trokhan et al. | 162/296 |
| 5,506,030 | 4/1996 | Landers et al. | 428/143 |
| 5,529,664 | 6/1996 | Trokhan et al. | 162/109 |
| 5,618,610 | 4/1997 | Tomita et al. | 428/152 |
| 5,623,888 | 4/1997 | Zafiroglu | 112/414 |
| 5,635,275 | 6/1997 | Biagioli et al. | 428/132 |
| 5,654,076 | 8/1997 | Trokhan et al. | 428/131 |
| 5,756,112 * | 5/1998 | Mackey | 424/402 |
| 5,914,177 * | 6/1999 | Smith, III et al. | 428/195 |
| 5,948,540 * | 9/1999 | Mackey et al. | 428/447 |

WIPING ARTICLE WHICH EXHIBITS DIFFERENTIAL WET EXTENSIBILITY CHARACTERISTICS

This application claims benefit to provisional application 60/073,443 filed Feb. 2, 1998.

FIELD OF THE INVENTION

The present invention relates to disposable wiping articles, towelettes, paper toweling, and the like. More particularly, this invention relates to disposable wipes having a plurality of wet extensible regions of increased caliper and texture when wetted.

BACKGROUND OF THE INVENTION

Disposable wiping articles are well known in the art. Such wiping articles typically have a substrate which includes one or more materials or layers. The substrate can be pre-moistened with a wetting agent prior to use, or alternatively, can be combined with a liquid at the point of use of the article. Pre-moistened wiping articles are also referred to as "wet wipes" and "towelettes."

Desirable features of such wiping articles include texture, caliper (thickness) and bulk (volume per unit weight). A relatively high value of texture is desirable for aiding in cleaning of surfaces. Wipe structures that result in increased texture upon wetting are particularly beneficial. Such structures may be achieved by utilizing multiple layers having differential wet extensibility. One such structure is disclosed in U.S. Pat. No. 4,469,735 issued Sep. 4, 1984 to Trokhan. However, increased texture does not necessarily produce increased caliper. Relatively high values of caliper and bulk are desirable for providing volume in the article for receiving and containing liquids.

Other methods of increasing texture by employing the principle of differential extensible layers are known, including the use of plastic webs as a relatively inextensible layer joined to creped paper. Nonwovens may also be joined to creped paper, the nonwoven serving as the constraining ply. In general, all that is necessary is one web which serves as a constraining ply, selectively joined to at least one other wet-extensible web. Upon wetting, unbonded portions of the wet-extensible web are deformed out of the plane of the wipe, thereby increasing caliper and texture. While these structures may provide desired caliper, bulk, and texture, they all require the use of at least two webs or plies with different extensibility properties to be joined into a multi-ply wipe.

Accordingly, it would be desirable to provide a disposable wiping article which provides improved texture and bulk while not requiring the use of multiple plies.

Additionally, it would be desirable to provide a disposable wiping article exhibiting the property of increased bulk and texture upon wetting while not requiring the use of a constraining ply.

Additionally, it would be desirable to provide a disposable wiping article which is reinforced for added wet and dry durability through the use of a polymer network.

Further, it would be desirable to provide a disposable wiping article comprising two or more plies, each of which exhibit the property of increased bulk and texture upon wetting while not requiring the use of a constraining ply.

SUMMARY OF THE INVENTION

The present invention provides a disposable wiping article (wipe). The wiping article may be single-layer (single-ply), or multi-layer (multi-ply). At least one layer (the only layer in a single-layer wiping article) is a primary layer and is wet extensible. A discontinuous coating is applied to selected portions of the wet extensible primary layer and cured to form a constraining component which inhibits wet extension of the primary layer in the plane of the primary layer. As a result, the primary layer deforms, such as by buckling or puckering, in the Z-direction (perpendicular to the plane of the primary layer), resulting in increased caliper, bulk, and texture. In one embodiment, more than one primary layer may be used in a single wiping article.

By applying a discontinuous coating to selected portions of the primary layer in a predetermined pattern, a plurality of uncoated regions are formed. In particular a continuous network pattern can be formed. The uncoated regions of the primary layer can each include a circular area 2002 (FIG. 1) inscribed within the bonding pattern wherein the diameter D of the inscribed circular area is at least 0.1 inch, more preferably at least about 0.2 inch, and most preferably at least about 0.4 inch. The diameter is preferably less than about 3.0 inches, and in one embodiment is less than about 2.0 inches.

The primary layer preferably can have a wet extensibility of at least about 4 percent, more preferably at least about 10 percent, more preferably at least about 20 percent, and still more preferably at least about 25 percent as measured using the "Wet Extensibility Test" provided below. The primary layer can be foreshortened, e.g., by creping, to provide the desired wet extensibility. In one embodiment, the primary layer comprises a wet laid, apertured paper web which is foreshortened at least about 30 percent, for example by dry creping.

The constraining component can be a hot melt adhesive, and is preferably an ethylene vinyl acetate (hereinafter EVA) hot melt adhesive (one suitable adhesive is a hot melt commercially available as H1382-01 from Ato-Findley Adhesives of Wauwatosa, Wis.). The adhesive provides the function of a constraining ply while allowing substantial variations in pattern and appearance. The continuous network also provides additional strength to the primary layer, as well as any additional layers.

The article may comprise additional webs or components which do not effect the functionality of the primary web or the constraining component. In one embodiment, the article comprises a high internal phase inverse emulsion.

The article can comprise a wetting agent prior to use of the article, which provides wetting of the primary layer. The wetting agent can be an aqueous lotion.

Alternatively, the article can comprise a relatively dry article which may or may not be wetted in use.

DETAILED DESCRIPTION OF THE INVENTION

Figure 1:
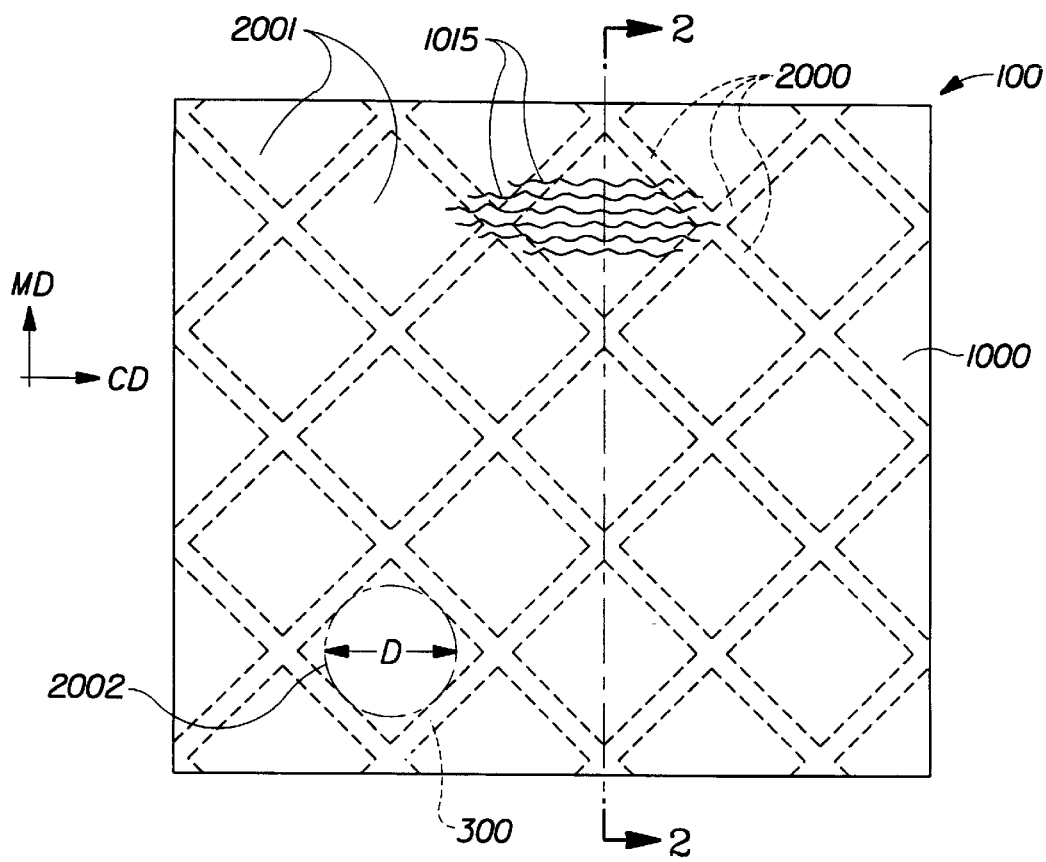
FIG. 1 is a plan view of a wipe of the present invention.

FIG. 1 is a plan view of a wipe 100 of the present invention. Wipe 100 comprises at least two components; a primary layer or ply 1000 and a constraining component 300. Primary layer 1000 is extensible when wetted, i.e., primary layer 1000 is wet extensible. By "wet extensible" it is meant that a material has a tendency to elongate in at least one direction when wetted. In general, "wetted" refers to wetting with aqueous solutions, including water, capable of inducing extension in the extensible primary layer. For example, water relaxes the crepe in foreshortened paper, thereby causing an extension of the paper in at least one direction in the plane of the paper. While not wishing to bound by theory, the relaxation of crepe may be a result of the loss of hydrogen bonds within the paper structure due to the presence of water. However, any fluid, mixture, or solution which could cause this crepe relaxation would be considered to "wet" the article. Extensibility is measured according to the "Wet Extensibility Test" described below.

Constraining component 300 can be a polymer applied in a melt state to selected portions of the wet extensible primary layer and cured to form a less wet extensible network 2000, that is, less wet extensible than primary layer 1000. The application of network 2000 can be described as coating the primary layer 1000 with a discontinuous coating. The coating is discontinuous because certain portions of wipe 100 must be left uncoated, and free to buckle out of plane upon wetting. For example, in FIG. 1, uncoated portions 2001 are formed by the network of the constraining component 2000.

In a preferred embodiment, network 2000 is a continuous network. As used herein, "continuous network" refers to a macroscopic pattern of the constraining component, i.e., the pattern appears to be continuous, forming a grid or net-like pattern and defining distinct, discrete uncoated regions.

In a preferred embodiment shown in FIG. 1, the coated regions are shown as a continuous network 2000 of intersecting lines forming generally diamond-shaped uncoated regions 2001. The width and spacing of the intersecting lines of the bonded regions may be adjusted to provide a desired pattern, that is, a desired size and spacing of diamond-shaped unbonded regions 2001. The continuous network of intersecting lines may be virtually any pattern, resulting in uncoated regions of virtually limitless shapes, including, for example, squares, rectangles, and triangles. Additionally, bonded regions can comprise generally parallel bands of coated regions separated by bands of uncoated regions. Other configurations are contemplated, for example, locally continuous coated regions, such as discrete circular bands and the like.

Because the continuous network 2000 is less extensible when wetted than the primary layer 1000, it serves the purpose of a constraining member to constrain extension of the primary layer 1000 in the plane of the primary layer when wetted. As a result, the primary layer 1000 deforms, such as by buckling or puckering, in the Z-direction, thereby increasing the caliper, bulk and texture of wipe 100. Additionally, because preferred polymer coatings are hot melt adhesives, the coated regions and uncoated regions are referred to herein as bonded regions and unbonded regions respectively. Bonds are formed between the adhesive and the primary layer, thereby constraining the primary layer in the bonded regions, thus not permitting wet extension in such regions. Primary layer 1000 is, however, free to extend out of plane in the unbonded regions, thereby producing a puckered, quilted effect in wipe 100 upon wetting.

Figure 2:
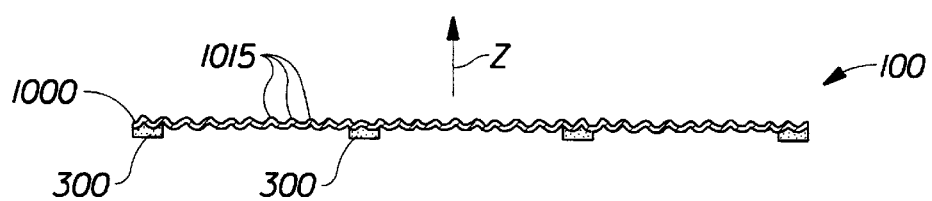
FIG. 2 is a cross section taken through Section 2—2 in FIG. 1, showing a wipe of the present invention before wetting.

FIG. 2 shows a cross section taken through Section 2—2 in FIG. 1, showing a single layer wipe of the present invention before wetting. Primary layer 1000 can be foreshortened and is preferably creped paper, having crepe ridges formed during manufacture, for example by creping off a Yankee dryer as part of the papermaking process. Adhesive 300 is applied in selected portions of primary layer 1000, and serves as the constraining member to constrain wet extension of primary layer upon wetting.

Figure 3:
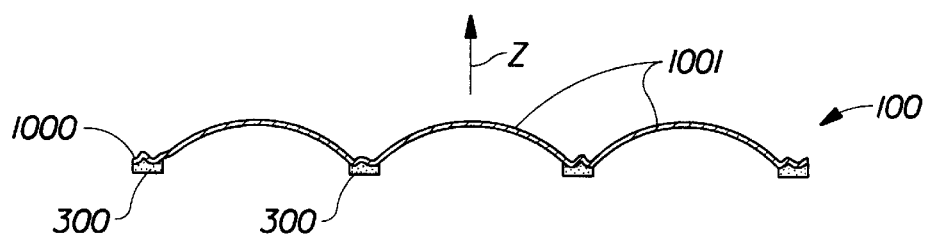
FIG. 3 is a cross section taken through Section 2—2 in FIG. 1, showing a wipe of the present invention after wetting.

FIG. 3 shows a cross section taken through Section 2—2 in FIG. 1, showing a single layer wipe of the present invention after wetting. Unbonded, i.e., unconstrained, regions 2001 of primary layer 1000 extend, but due to the constraint imposed by continuous network 2000 as a constraining member, extension results in out-of-plane deformation, forming dome-like protuberances 1001, which increase the wet texture, wet caliper (thickness) and wet bulk of the article 1000. The wipe 100 can have a wet caliper to dry caliper ratio greater than 1.0, and more preferably at least about 1.1, and even more preferably at least about 1.2, where the wet to dry caliper ratio is a relative measure of the wet and dry thickness of the article. The wet to dry caliper ratio is measured according to the procedure set forth below.

Figure 4:
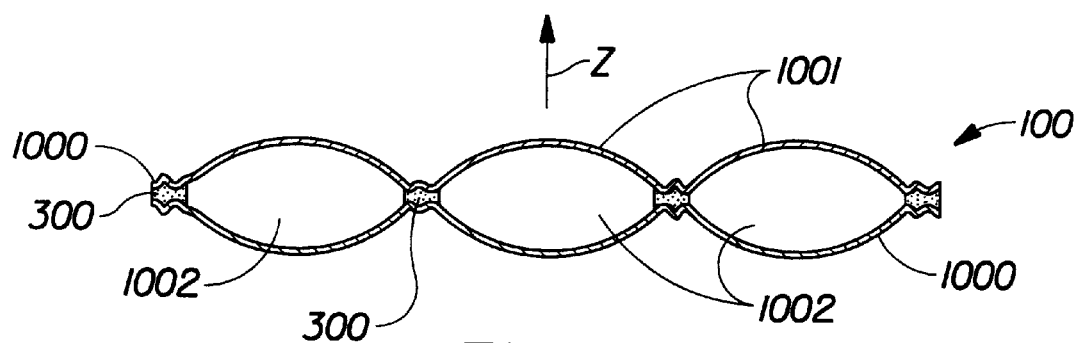
FIG. 4 is a cross section of one embodiment of the present invention wherein comprising two plies of an extensible cellulosic web joined by a constraining member (after wetting).

FIG. 4 depicts a cross section of one embodiment wherein the article may comprise two primary layers 1000, i.e., two plies of a wet extensible cellulosic web, joined by a shared constraining member, such as an adhesive network. In this embodiment, dome-like protuberances 1001 form pockets 1002, which can serve to contain wetting agents, cleansers, and the like. Alternatively, pockets 1001 can serve to entrap dirt and other particulates gathered during wiping with the wipe. When formed into a two-layer (or two ply) structure, the web of the present invention can have a wet caliper to dry caliper ratio greater than about 1.4.

The primary layer can comprise a high internal phase emulsion, which during use can provide an aqueous solution enabling wet extension of the primary layer, as described more fully below. For example, the high internal phase emulsion can be applied to one side of wipe 100 as a continuous coating or discontinuous stripes, spots, and the like. Upon use, wetting agents can be released, allowing wet extensibility with the resulting increase in bulk and texture of wipe 100.

Primary Layer

Suitable materials from which primary layer 1000 can be formed include woven materials, nonwoven materials, foams, battings, and the like. The fibers or filaments of the primary layer 1000 can be natural (e.g. cellulosic fibers such as wood pulp fibers, cotton linters, and bagasse fibers) or synthetic (e.g. polyolefins, polyamides, polyesters, or rayon).

Primary layer 1000 should be constructed to have a wet extensibility of at least 4 percent, more preferably at least about 10 percent, and still more preferably at least about 20 percent. In one embodiment, the first layer has a wet extensibility of at least about 30 percent. Preferably, the difference between the wet extensibility of the first layer and the wet extensibility of the second layer (the wet extensibility of the second layer subtracted from the wet extensibility of the first layer) is at least about 4 percent, more preferably at least about 10 percent, and still more preferably at least about 30 percent.

The first layer can be foreshortened, e.g., by creping, to provide the desired wet extensibility. Therefore, the primary layer 1000 can comprise a wetlaid paper web of cellulosic wood pulp fibers which is foreshortened at least about 4 percent, more preferably at least about 10 percent, and still more preferably at least about 20 percent. In one embodiment, the primary layer comprises a wet laid cellulosic paper web which is foreshortened at least about 35 percent by dry creping off a Yankee dryer during papermaking.

Referring to FIG. 1, the primary layer 1000 comprises crepe ridges 1015 corresponding to the foreshortening of the primary layer 1000. In FIG. 3 the crepe ridges 1015 are not shown to indicate that the dry creping has been drawn out upon wetting and extension of the primary layer 1000. However, it is not necessary that all the crepe be drawn out; partial extension results in caliper increase as well.

The first layer 1000 can have a basis weight of between about 15 and about 65 grams per square meter (gsm), and a caliper between about 4 mils (0.004 inch) and about 40 mils (0.040 inch). The first layer can comprise a paper web made according to the methods described in one or more of the following patents which are incorporated herein by reference: U.S. Pat. No. 3,301,746 (Sanford); U.S. Pat. No. 3,994,771 (Morgan) U.S. Pat. No. 4,300,981 (Carstens); U.S. Pat. No. 4,529,480 (Trokhan); U.S. Pat. No. 5,073,235 (Trokhan); U.S. Pat. No. 5,506,715 (Trokhan); U.S. Pat. No. 4,637,859 (Trokhan); U.S. Pat. No. 5,364,504 (Smurkoski et al.); and U.S. Pat. No. 5,529,664 (Trokhan et al.).

In one embodiment, the first layer 1000 comprises a paper web having multiple regions distinguished from one another by basis weight. The web can have a continuous high basis weight network, and discrete regions of low basis weight which circumscribe discrete regions of intermediate basis weight. Such a paper web is disclosed in U.S. Pat. No. 5,245,025 issued to Trokhan et al. on Sep. 14, 1993, which patent is incorporated herein by reference.

While not wishing to be bound by theory, it is believed that the paper strength can significantly alter the overall appearance of the complete article. The amount of foreshortening, such as by creping, of the first layer is proportional to the amount of planar expansion and thereby the amount of caliper generated upon wetting. However, if the wet strength of the paper article is insufficient, the "buckles" may collapse to form a more "wrinkled" product having less caliper. Therefore both crepe and wet strength can be adjusted to provide an amount of texture based on the intended use of the article. Wet burst measurements were measured by a Thwing-Albert Burst Tester model number 1300-77, which tested peak load of a fully wetted substrate. The test utilized a 0.5 in ball diameter, a 5 in/min ball velocity, and clamps the test sample around a 3.5 in. diameter circle perpendicular to the motion of the ball. Peak load wet burst strengths are between 100 and 1200 grams per ply. More preferably between 400 and 700 grams per ply and most preferably between 500 and 600 grams per ply.

Constraining Component

Selected portions of the primary layer 1000 are coated with a discontinuous coating in a predetermined pattern to provide a plurality of coated and uncoated regions on the primary layer 1000. In FIGS. 1–3, the coated regions are designated 2000, and the uncoated regions are designated 2001. The coated regions form a constraining component that serves to constrain the primary layer and inhibit wet extension upon wetting of the web of the present invention.

The term "bonding" can be used to describe the coating because in a preferred embodiment an adhesive is applied to form the discontinuous coated regions. Suitable adhesives can be applied by methods known in the art. Exemplary methods include various methods of printing, spraying, extruding, slot coating, roll transfer methods. In particular, in a preferred embodiment, adhesive 300 is applied by printing methods, such as gravure printing, reverse gravure printing, screen printing, flexographic printing, and the like. In one preferred embodiment, EVA hot melt adhesive may be screen printed in a lattice pattern generally as shown as 2000 in FIG. 1. The suitable screen for this embodiment is a 40 mesh Galvano screen manufactured by Rothtec Engraving Corp., New Bedford, Mass.

The adhesive used is preferably water insoluble so that multi-layer articles (as shown in FIG. 4) can be wetted with water for longer periods without delamination of the primary and second layers. The adhesive is preferably also surfactant tolerant. By "surfactant tolerant" it is meant that the bonding characteristics of the adhesive are not degraded by the presence of surfactants. Suitable adhesives include EVA (ethylene vinyl acetate) based hot melt adhesives. One suitable adhesive is a hot melt adhesive commercially available as H1382-01 from Ato-Findley Adhesives of Wauwatosa, Wis.

In a preferred embodiment constraining component 300 is hot melt adhesive. The adhesive is applied to selected portions of the primary layer 1000 and other layers, if used, in a predetermined bonding pattern, preferably with an EVA hot melt adhesive (one suitable adhesive is a hot melt commercially available as H1382-01 from Ato-Findley Adhesives of Wauwatosa, Wis.). The bonding pattern will be described with reference to the primary layer 1000, with the understanding that the description can also apply to other patterns, as well as multiple layer embodiments such that the additional layers do not affect the essential characteristics of the primary layer.

Referring to FIG. 1, the bonded areas of the primary layer 1000 form a continuous network bonding pattern 2000. The continuous network pattern defines discrete, unconnected unbonded regions 2001. In FIG. 1, the unbonded regions 2001 are in the shape of diamonds, but it will be understood that the regions 2001 could also have other shapes, including but not limited to circles, squares, ovals, triangles, as well as other regular and irregular polygons, and the like. As well, the network need not be completely continuous, nor limited to a pattern of straight or uniform lines, but may, for example, be a network resulting in circular, oval, or other non-polygonal shapes. Further, it is contemplated that the continuous network need not cover the entire surface of the wipe, but can be applied in localized, smaller areas where caliper generation is desired.

The unbonded regions 2001 of the primary layer 1000 can each include a circular area inscribed within the bonding pattern. The diameter D of the inscribed circular area 2002 should be at least 0.1 inch. The diameter D should be at least 0.1 inch in order to generate a sufficient increase in caliper and bulk of the article 100 when the primary layer 1000 is wetted. Preferably, the diameter D is at least 0.2 inch, and most preferably at least 0.4 inch. The diameter D is preferably less than 3.0 inches to provide visually distinct protuberances 1001, and to provide protuberances 1001 without excessive wrinkling. In one embodiment the diameter D is less than 2.0 inch.

With reference to FIG. 1, a hot melt adhesive 300 can be applied to primary layer 1000 in a continuous network defining a discontinuous plurality of unbonded regions 2001. In one preferred embodiment, as shown in FIG. 1, the adhesive 300 is applied as parallel, spaced apart lines in a first direction, intersected by parallel, spaced apart lines in a second direction. The intersecting lines can form diamond-shaped patterns of unbonded regions 2001 in the final wipe 100. In the embodiment shown in FIG. 1, the hot melt adhesive 300 can be applied in lines having a width of less than about 0.5 inch, preferably less than about 0.05 inch, and can be less than about 0.1 inch. The spacing between adjacent lines of adhesive can be less than about 2.0 inches, preferably about 1.0 inches, and can be less than about 0.5 inch.

The hot melt adhesive can be applied to primary layer 1000 in bands which extend generally parallel to the machine direction, MD, of primary layer 1000. The hot melt adhesive can be applied in stripes having a width of about 0.125 inch to about 1 inch. The spacing between adjacent adhesive stripes can be about 0.125 inch to about 2 inches. In this configuration, the bands of adhesive form a constraining member comprising discrete (i.e., not continuous) portions that nevertheless serve to constrain the wet extensible primary layer from extending in the direction of the bands. For example, for bands that extend in the machine direction, wet extension of the primary layer in the machine direction would be inhibited, thereby causing the desired wet bulk as the primary layer buckles in the Z direction.

Other Components

In certain embodiments it may be desirable to add additional components, including additional layers, to the primary layer 1000 of the present invention. In certain embodiments it may even be desirable to place two primary layers together, with or without other wipe components disposed between, as shown in FIG. 4. For example, an additional, secondary layer having differing wet extensibility may be desirable. Suitable materials from which the secondary layer can be formed include woven materials, nonwoven materials, foams, battings, and the like. Particularly preferred materials are nonwoven webs having fibers or filaments distributed randomly as in "air-laying" or certain "wet-laying" processes, or with a degree of orientation, as in certain "wet-laying" and "carding" processes.

One material from which a second layer can be formed is a nonwoven web formed by hydroentanglement of fibers. A suitable hydroentangled web is a nonwoven, hydroentangled web comprising about 50 percent by weight rayon fibers and about 50 percent by weight polyester fibers, and having a basis weight of about 62 grams per square meter. A suitable hydroentangled nonwoven web is commercially available from PGI Nonwovens of Benson, N.C. under the designation CHICOPEE 9931.

As shown in FIG. 4, two primary layers may be joined by a common constraining member, such as continuous adhesive network 300, to form a wipe of the present invention having dome-like protuberances 1001 on both sides of the wipe. Each primary layer 1000 could have different amounts of foreshortening, so as to produce different wet extensibility characteristics. By having different crepe percentages, for example, a wetted wipe as shown in FIG. 4 could have a more textured side and a less textured side in a single wipe.

Figure 5:
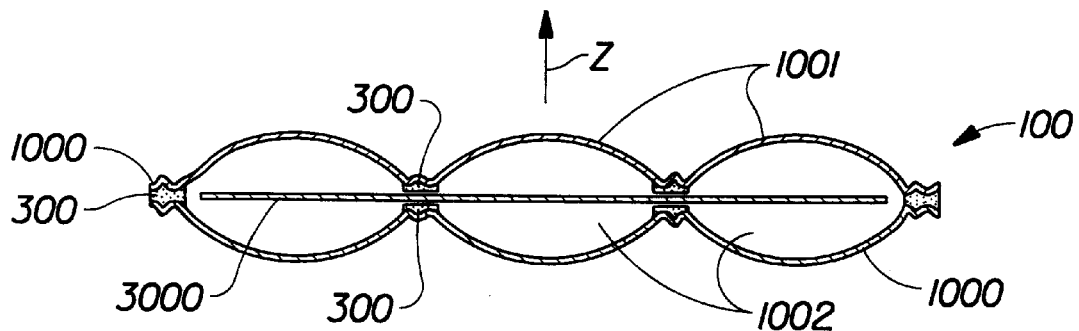
FIG. 5 is a cross section of one embodiment wherein the article comprises a lotion disposed intermediate a first and second wet extensible webs, after wetting.

FIG. 5 shows schematically one embodiment of the present invention comprising a cleaning aid 3000 disposed between first and second primary layers. The two primary layers can be joined at portions, for example at the lateral edges, but are otherwise not joined, i.e., they do not share a constraining member. A cleaning aid 3000 may be enclosed as shown, and may be a continuous coating of a lotion applied to the first primary layer prior to joining with the second primary layer. The cleaning aid 3000 may be a wetting agent, a sudzing agent, or other lathering agent such as a surfactant.

In a preferred embodiment, cleaning aid 3000 is a high internal phase inverse emulsion applied as a continuous coating, discontinuous strips, spots, or other pattern and enclosed by first and second plies of a primary web 1000, that is, two plies of a wet extensible material. The high internal phase emulsion allows the wipe to be stored in a dry state, with wetting occurring upon use. A preferred emulsion comprises: (1) a continuous solidified lipid phase; (2) an emulsifier that forms the emulsion when the lipid phase is liquid; and (3) an internal polar phase dispersed in the lipid phase. In particular, suitable emulsions are described in detail in commonly assigned, co-pending U.S. patent application Ser. No. 08/430,061, filed Apr. 27, 1995 by L. Mackey, now abandoned, or commonly assigned co-pending U.S. patent application Ser. No. 640,268, filed Apr. 30, 1996 by L. Mackey and B. Hird, now abandoned, both of which are incorporated by reference herein. The high internal phase inverse emulsions of the present invention can also comprise other optional components typically present in moisture containing solutions of this type. These optional components can be present in either the continuous lipid phase or the internal polar phase and include perfumes, antimicrobial (e.g., antibacterial) actives, pharmaceutical actives, deodorants, opacifiers, astringents, skin conditioners, cosmetics, cleansers, surface conditioners, insect repellents, pH buffers, and the like, as well as mixtures of these components. All of these materials are well known in the art as additives for such formulations and can be employed in effective, appropriate amounts in the emulsions of the present invention. A particularly preferred optional component that is included the emulsions of wet-like cleansing wipes according to the present invention is glycerin as a skin conditioning agent.

Figure 6:
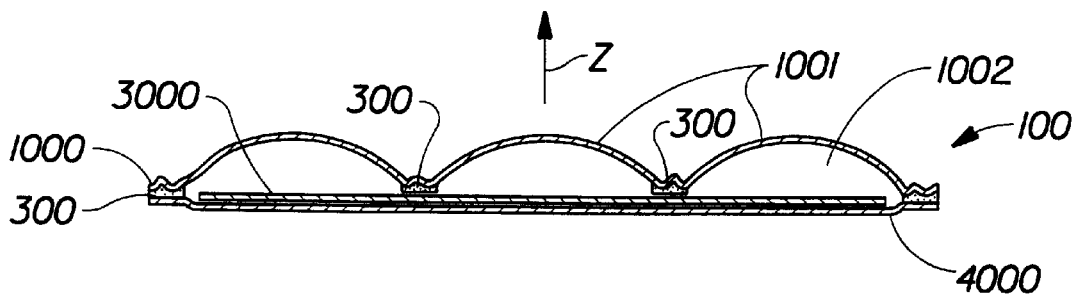
FIG. 6 is a cross section of one embodiment wherein the article comprises a lotion disposed intermediate one ply of a primary web and a second ply of a nonwoven web, after wetting.

Other configurations incorporating lotions, surfactants, cleansers, and the like are contemplated. For example, FIG. 6 depicts in cross-section another embodiment of a wetted wipe of the present invention wherein the lotion is disposed intermediate one ply of a primary web 1000 and a second ply of a nonwoven web 4000.

Wet Extensibility Test

The wet extensibility of a layer, such as the layer 100 or the layer 200, is determined using the following procedure. Samples are conditioned at 70 degrees Fahrenheit and 50 percent relative humidity for two hours prior to testing.

First, the direction of greatest wet extensibility in the plane of the layer is determined. For dry creped paper webs, this direction will be parallel to the machine direction, and generally perpendicular to the crepe ridges.

If the direction of greatest wet extensibility is not known, the direction can be determined by cutting seven samples from a sheet with sample lengths oriented between 0 degrees and 90 degrees, inclusive, with respect to a reference line drawn on the sheet. The samples are then measured as set forth below to determine the direction of greatest wet extensibility.

Once the direction of the greatest wet extensibility is determined, 8 samples are cut to have a length of about 7 inches measured parallel to the direction of greatest wet extensibility, and a width of at least 1 inch. The samples are cut from unbonded portions of the layers 100 and 200, or, if unbonded portions having the above dimensions cannot be cut from the article 20, then samples are cut from the layers 100 and 200 prior to bonding the layers together. Two marks are placed on each sample, such as with an ink pen. The marks are spaced apart 5 inches as measured parallel to the direction of greatest wet extensibility. This 5 inch length is the initial dry test length of the sample.

Each sample is thoroughly wetted by submerging the sample in distilled water for 30 seconds in a water bath. Each sample is removed from the water bath and immediately supported to hang vertically so that a line through the two marks is generally vertical. The wet sample is supported such that the support does not interfere with extension between the two marks (e.g. with a clip which does not contact the sample between the two marks). The wet test length of the sample is the distance between the two marks. The distance is measured within 30 seconds of removing the sample from the water bath.

For each sample, the percent wet extension is calculated as

Sample Wet Extension=(wet test length−initial dry test length)/(initial dry test length)×100

For example, for a measured wet test length of 6.5 inches and an initial dry test length of 5.0 inches, the wet extension is ((6.5−5)/5)×100=30 percent.

The wet extensibility of the samples is the average of 8 calculated values of sample wet extension.

Wet Caliper to Dry Caliper Ratio

The wet caliper to dry caliper ratio is measured using a Thwing-Albert Instrument Co. Electronic Thickness Tester Model II, using the following procedure. Samples are conditioned at 70 degrees Fahrenheit and 50 percent relative humidity for two hours prior to testing.

The dry caliper of the article 20 is measured using a confining pressure of 95 grams per square inch and a load foot having a diameter of 2 inches. The dry caliper is measured for eight samples. For each sample, the caliper is measured with the load foot centered on an unbonded region of the first layer 100. The eight caliper measurements are averaged to provide an average dry caliper.

Each sample is then wetted by submerging the sample in a distilled water bath for 30 seconds. The sample is then removed from the water bath and drained by hanging vertically for about five seconds. The caliper of the wet sample is measured within 30 seconds of removing the sample from the bath. The wet caliper is measured in the same location in which the dry caliper was previously measured. The eight wet caliper measurements are averaged to provide an average wet caliper. The wet caliper to dry caliper ratio is the average wet caliper divided by the average dry caliper.

What is claimed is:

1. A single layer disposable wiping article comprising:
   (a) a primary layer, the primary layer being extensible in the plane of the primary layer when the primary layer is wetted; and
   (b) a discontinuous coating applied to at least one side of the primary layer defining coated regions and a plurality of uncoated regions, the coating being less extensible when wetted than the primary layer;
wherein selected portions of the primary layer are constrained by a network of coated regions thereby inhibiting wet extension of the primary layer in the plane of the primary layer, and wherein portions of the primary layer in the uncoated regions exhibit out-of-plane deformation upon wetting, and wherein the article has a wet caliper to dry caliper ratio of greater than about 1.0.

2. The article of claim 1, wherein the discontinuous coating forms a continuous network.

3. The article of claim 1, wherein the unbonded regions of the primary layer each comprise an inscribed circular area, and wherein the diameter of the inscribed circular area is between about 0.1 inch to about 3.0 inch.

4. The article of claim 1, wherein the primary layer comprises a foreshortened cellulosic web.

5. The article of claim 4, wherein said foreshortened cellulosic web is formed by wet microcontraction techniques.

6. The article of claim 4, wherein said foreshortened cellulosic web is creped.

7. The article of claim 1, wherein the primary layer has a wet extensibility of at least about 4 percent.

8. The article of claim 1, wherein the primary layer has a wet extensibility of at least about 10 percent.

9. The article of claim 1, wherein the primary layer has a wet extensibility of at least about 20 percent.

10. The article of claim 1, wherein the primary layer has a wet extensibility of at least about 25 percent.

11. The article of claim 1, having a wet caliper to dry caliper ratio greater than about 1.2.

12. A multiple layer disposable wiping article comprising:
    (a) a first primary layer, the first primary layer being extensible in the plane of the first primary layer when the first primary layer is wetted; and
    (b) a second primary layer joined to the first primary layer in a face to face relationship by a discontinuous coating applied to at least one side of the primary layer defining coated regions and a plurality of uncoated regions;
wherein the article has a wet caliper to dry caliper ratio greater than about 1.4.

13. The article of claim 12, wherein the discontinuous coating forms a continuous network.

14. The article of claim 13, wherein the unbonded regions of the primary layer each comprise an inscribed circular area, and wherein the diameter of the inscribed circular area is between about 0.1 inch to about 3.0 inch.

15. The article of claim 12, wherein the first and second primary layers comprise a foreshortened cellulosic web.

16. The article of claim 12, wherein the primary layer has a wet extensibility between at least about 4 percent and at least about 25 percent.

17. The article of claim 12, wherein the second primary layer comprises a nonwoven web.

18. The article of claim 12, further comprising a lotion disposed on at least one of the first or second primary layers.

* * * * *